United States Patent
Harmouche (10) Patent No.: US 12,226,138 B2
(45) Date of Patent: Feb. 18, 2025

(54) CRYOBALLOON DEFLATION ASSEMBLY AND METHOD

(71) Applicant: Boston Scientific Scimed Inc, Maple Grove, MN (US)

(72) Inventor: Chadi Harmouche, Saint-Laurent (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 331 days.

(21) Appl. No.: 16/696,192

(22) Filed: Nov. 26, 2019

(65) Prior Publication Data

US 2020/0093531 A1 Mar. 26, 2020

Related U.S. Application Data

(63) Continuation of application No. PCT/US2018/032355, filed on May 11, 2018.

(Continued)

(51) Int. Cl.
*A61B 18/02* (2006.01)
*A61B 18/00* (2006.01)

(52) U.S. Cl.
CPC .... *A61B 18/02* (2013.01); *A61B 2018/00255* (2013.01); *A61B 2018/00351* (2013.01);
(Continued)

(58) Field of Classification Search
CPC .......... A61B 2018/00255; A61B 2018/00351; A61B 2018/00577; A61B 2018/0212; A61B 2018/0262; A61B 18/02; A61B 2018/00214; A61B 2018/0022; A61B 2018/00285; A61B 2018/00375;
(Continued)

(56) References Cited

U.S. PATENT DOCUMENTS

| | | | |
|---|---|---|---|
| 2001/0034469 A1 | 10/2001 | Nigroni et al. | |
| 2005/0187546 A1* | 8/2005 | Bek | A61B 5/06 606/41 |
| 2005/0246646 A1* | 11/2005 | Beam | G06F 3/0481 715/833 |
| 2006/0116549 A1 | 6/2006 | Sekiguchi et al. | |
| 2006/0129142 A1* | 6/2006 | Reynolds | A61B 18/02 606/21 |
| 2009/0088735 A1* | 4/2009 | Abboud | A61B 18/02 606/22 |
| 2011/0092967 A1* | 4/2011 | Harvey-Poncelet | A61M 25/10185 604/246 |

(Continued)

OTHER PUBLICATIONS

International Search Report and Written Opinion received for PCT Patent Application No. PCT/US2018/032355, mailed on Aug. 8, 2018, 6 pages.

*Primary Examiner* — Daniel W Fowler
*Assistant Examiner* — Bradford C. Blaise
(74) *Attorney, Agent, or Firm* — Nelson Mullins Riley & Scarborough LLP (57) ABSTRACT

A cryoballoon deflation assembly for an intravascular catheter system for use during a cryoablation procedure includes a first deflation initiator and a first deflation initiator inhibitor. The first deflation initiator is configured to automatically activate a vacuum pump to deflate a cryoballoon upon completion of a stage of the cryoablation procedure. The first deflation initiator inhibitor is manually changeable to between an activated and deactivated state. When in the activated state, the first deflation initiator inhibitor is configured to inactivate the first deflation initiator. The cryoballoon deflation assembly can further include a second deflation initiator. The second deflation initiator is manually changeable between an activated and deactivated state. When in the activated state, the second deflation initiator is triggered to activate the vacuum pump to deflate the cryoballoon.

10 Claims, 5 Drawing Sheets

Related U.S. Application Data (60) Provisional application No. 62/545,348, filed on Aug. 14, 2017, provisional application No. 62/512,364, filed on May 30, 2017.

(52) U.S. Cl.
CPC ............... *A61B 2018/00577* (2013.01); *A61B 2018/0212* (2013.01); *A61B 2018/0262* (2013.01)

(58) Field of Classification Search
CPC .. A61B 2018/00916; A61B 2018/0094; A61B 2018/00946; A61B 2018/00952; A61B 2018/00958
See application file for complete search history.

(56) References Cited

U.S. PATENT DOCUMENTS

| | | |
|---|---|---|
| 2012/0089047 A1 | 4/2012 | Ryba et al. |
| 2013/0150693 A1 | 6/2013 | D'Angelo et al. |
| 2014/0024955 A1 | 1/2014 | Zhadkevich |
| 2015/0088113 A1* | 3/2015 | Clark ..................... A61B 18/02 606/21 |
| 2015/0165173 A1 | 6/2015 | Helkowski et al. |
| 2015/0187546 A1 | 7/2015 | Furukawa et al. |
| 2015/0201956 A1* | 7/2015 | Higgins ......... A61B 17/320758 606/159 |
| 2017/0007310 A1* | 1/2017 | Rajagopalan ........ A61B 5/0084 |
| 2019/0076152 A1* | 3/2019 | Franklin .......... A61B 17/12036 |

* cited by examiner

CRYOBALLOON DEFLATION ASSEMBLY AND METHOD

CROSS-REFERENCE TO RELATED APPLICATION

This application is a continuation of International Application No. PCT/US18/032355, filed on May 11, 2018 and entitled "CRYOBALLOON DEFLATION ASSEMBLY AND METHOD," which claims the benefit of U.S. Provisional Application No. 62/512,364 filed on May 30, 2017 and entitled "CRYOBALLOON DEFLATION ASSEMBLY AND METHOD" and U.S. Provisional Application No. 62/545,348 filed on Aug. 14, 2017 and entitled "DEVICE AND METHOD FOR MANUALLY DEFLATING A CRYOBALLOON." As far as permitted, the contents of International Application No. PCT/US18/032355 and U.S. Provisional Application Nos. 62/512,364 and 62/545,348 are incorporated in their entirety herein by reference.

TECHNICAL FIELD

The present disclosure relates to medical devices and methods for performing cryoablation procedures. More specifically, the disclosure relates to devices and methods for controlling deflation of a cryoablation catheter.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few.

In particular, catheter ablation involves delivering ablative energy to tissue inside the heart to block aberrant electrical activity from depolarizing heart muscle cells out of synchrony with the heart's normal conduction pattern. The catheter ablation procedure is performed by positioning a portion, such as a tip, of an energy delivery catheter adjacent to diseased or targeted tissue in the heart. The energy delivery component of the system is typically at or near the most distal (i.e., farthest from the operator or user) portion of the catheter, and often at the tip of the catheter.

Various forms of energy are used to ablate diseased heart tissue. These can include radio frequency, ultrasound and laser energy, to name a few. One form of energy that is used to ablate diseased heart tissue includes cryogenics (also referred to herein as "cryoablation"). During a cryoablation procedure, the tip of the catheter is positioned adjacent to targeted cardiac tissue, at which time energy is delivered in the form of a refrigerant or cryogenic fluid to create tissue necrosis, rendering the ablated tissue incapable of conducting electrical signals. The dose of energy delivered is a critical factor in increasing the likelihood that the treated tissue is permanently incapable of electrical conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis, while avoiding excessive energy leading to collateral tissue injury.

Atrial fibrillation, one of the most common arrhythmias, can be treated using catheter ablation. In the earliest stages of the disease, paroxysmal atrial fibrillation, the treatment strategy involves isolating the pulmonary vein(s) from the left atrial chamber of the heart. Recently, the use of techniques known as "balloon cryotherapy" catheter procedures to treat atrial fibrillation have increased. Some advantages of balloon cryotherapy include ease of use, shorter procedure times and improved patient outcomes.

During balloon cryotherapy, an inflated cryoballoon at the distal portion of the catheter is positioned against an ostium of a pulmonary vein to occlude the pulmonary vein from blood flow. In order to ensure effective positioning of the cryoballoon, it generally takes several minutes and the use of guiding tools, such as a fluoroscopy or ICE (inter-cardiac echo). The goal of balloon cryotherapy is to completely isolate one or more pulmonary veins of the patient by creating circumferential transmural lesions around the ostium of the pulmonary vein being treated. [0007] Balloon cryotherapy generally includes a thawing stage, which can be temperature based, time based, or both. As stated herein, during balloon cryotherapy the cryogenic fluid is injected into the cryoballoon in order to freeze the diseased heart tissue. Once treated, the diseased heart tissue is allowed to thaw to a certain temperature and/or for a certain period of time. During the thawing stage, the cryoballoons are generally maintained inflated to prevent tissue damage to the patient. With most catheters, after the thawing stage is completed, the cryoballoons can automatically deflate. However, automatic deflation of the cryoballoons after the thawing stage can increase the procedure time when ablations on the same pulmonary vein are to be performed due to the need to continually reposition the catheter and/or cryoballoons.

Additionally, once the ablations have been made to the satisfaction of the operator of the system, the catheter can be removed from the patient. In order for the cryoballoons to achieve a minimal profile it is beneficial that the cryoballoons be elongated before the cryoballoons are deflated. Accordingly, prior to removal, it is necessary to axially elongate and deflate the cryoballoons to allow for the cryoballoons to be retracted back into a catheter sheath. A vacuum source may be used to assist in cryoballoon deflation by removing or evacuating cryogenic fluid from the cryoballoons. Without elongation there is a higher likelihood that the act of only removing or evacuating the cryogenic fluid via the vacuum source will not adequately achieve a minimum profile of the cryoballoons for retraction into the catheter sheath.

Attempts to address this issue have not been altogether satisfactory. For example, a method has been used to elongate the cryoballoons that includes inserting a stiff wire down an existing guidewire which would engage the distal portion of a guidewire lumen by pushing on the stiff wire. The guidewire lumen would move distally, stretching the cryoballoons in the process. However, the stiff wire adds an extra component to the procedure that has no other function. Further, the guidewire lumen itself becomes more complex with the need to have the diameter of the distal portion of the guidewire lumen reduced in order to permit the stiff wire to engage and actuate the guidewire lumen.

Another attempt to address this issue includes a mechanical means by which the guidewire lumen is extended that does not require extra components for the procedure. However, this mechanical means also does not reliably provide the actual means to deflate the cryoballoons. In other words, there is no assurance that the cryoballoons have been elongated before the vacuum source collapses and/or deflates the cryoballoons. Unfortunately, it could therefore be possible for the operator to attempt to retract the cryoballoons into the catheter sheath without proper elongation, which could damage the cryoballoons and/or the catheter sheath, increase the time of the procedure and/or potentially injure the patient.

SUMMARY

The present invention is directed toward a cryoballoon deflation assembly (sometimes referred to herein as "deflation assembly") for an intravascular catheter system (sometimes referred to herein as "catheter system") for use during a cryoablation procedure. In various embodiments, the catheter system can include a vacuum pump and a cryoballoon. In certain embodiments, the deflation assembly includes a first deflation initiator and a first deflation initiator inhibitor. The first deflation initiator can be configured to automatically activate the vacuum pump to deflate the cryoballoon upon completion of a stage of the cryoablation procedure. The first deflation initiator inhibitor can be manually changeable between an activated state and a deactivated state. In some embodiments, the first deflation initiator inhibitor can be configured to inactivate the first deflation initiator when the first deflation initiator inhibitor is in the activated state.

In another embodiment, the catheter system can include a graphical display (also sometimes referred to as a graphical user interface or "GUI"). The first deflation initiator inhibitor can be configured to be positioned on the GUI. In one embodiment, the first deflation initiator inhibitor can include a switch that moves between a first position and a second position. In this embodiment, only one of the positions of the switch can inactivate the first deflation initiator. In another embodiment, the first deflation initiator inhibitor can include a control button that is configured to be depressed. In such embodiment, the first deflation initiator can be inactivated when the control button is depressed.

In other embodiments, the catheter system can include a handle assembly or a control console. The first deflation initiator inhibitor can be configured to be positioned on the handle assembly or the control console.

In some embodiments, the deflation assembly can further include a second deflation initiator. The second deflation initiator can be triggered when the first deflation initiator inhibitor is in the activated state. In certain embodiments, the second deflation initiator can also be configured to be manually changeable between an activated and deactivated state. In one embodiment, the second deflation initiator can activate the vacuum pump to deflate the cryoballoon when the second deflation initiator is in the activated state. In various embodiments, the second deflation initiator can be configured to be positioned on one of the handle assembly, the control console or the GUI.

In one embodiment, the second deflation initiator can include a switch that moves between a first position and a second position. In this embodiment, only one of the positions of the switch can activate the vacuum pump to deflate the cryoballoon. In another embodiment, the second deflation initiator can include a control button that is configured to be depressed. In such embodiment, the vacuum pump can be activated to deflate the cryoballoon when the control button is depressed.

In certain embodiments, the deflation assembly can further include a controller. The first deflation initiator inhibitor can send a first signal to the controller to inactivate the first deflation initiator when the first deflation initiator inhibitor is in the activated state.

The present invention is also directed toward a method for manually initiating deflation of a cryoballoon during a cryoablation procedure. The method can include the step of inactivating a first deflation initiator that is configured to automatically activate a vacuum pump to deflate the cryoballoon upon completion of a stage of the cryoablation procedure by manually setting a first deflation initiator inhibitor to an activated state.

In one embodiment, the step of inactivating can include moving a switch between a first position and a second position. Only one of the positions of the switch inactivates the first deflation initiator. In another embodiment, the step of inactivating can include depressing a control button. The first deflation initiator is inactivated when the control button is depressed.

In certain embodiments, the method can further comprise the step of triggering a second deflation initiator by manually setting the first deflation initiator inhibitor to an activated state.

In other embodiments, the method can further comprise the step of activating the vacuum pump to deflate the cryoballoon by manually setting the second deflation initiator to an activated state. In one embodiment, the step of activating can include moving a switch between a first position and a second position. Only one of the positions of the switch activates the vacuum pump to deflate the cryoballoon. In another embodiment, the step of activating can include depressing a control button. The vacuum pump is activated to deflate the cryoballoon when the control button is depressed.

In one embodiment, the step of inactivating can include sending a first signal with the first deflation initiator inhibitor when the first deflation initiator inhibitor is in the activated state to a controller to inactivate the first deflation initiator.

Additionally, in some applications, the present invention is directed toward a deflation assembly for an intravascular catheter system for use during a cryoablation procedure. The intravascular catheter system can include a GUI, a vacuum pump and a cryoballoon. The deflation assembly can include a controller, a first deflation initiator, a first deflation initiator inhibitor and a second deflation initiator. The first deflation initiator can be configured to automatically activate the vacuum pump to deflate the cryoballoon upon completion of a stage of the cryoablation procedure. The first deflation initiator inhibitor can be configured to be positioned on the GUI. In certain embodiments, the first deflation initiator inhibitor can be manually changeable between an activated and deactivated state. In one embodiment, the first deflation initiator inhibitor can send a first signal to the controller to inactivate the first deflation initiator when the first deflation initiator inhibitor is in the activated state. In various embodiments, the second deflation initiator can also be triggered when the first deflation initiator inhibitor is in the activated state. The second deflation initiator can also be configured to be manually changeable between an activated and a deactivated state. In one embodiment, the second deflation initiator can send a second signal to the controller to activate the vacuum pump to deflate the cryoballoon when the second deflation initiator is in the activated state While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Embodiments of the present invention are described herein in the context of an intravascular catheter system which includes a cryoballoon deflation assembly. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound and laser energy, as non-exclusive examples. The present invention is intended to be effective with any or all of these and other forms of energy.

Figure 1:
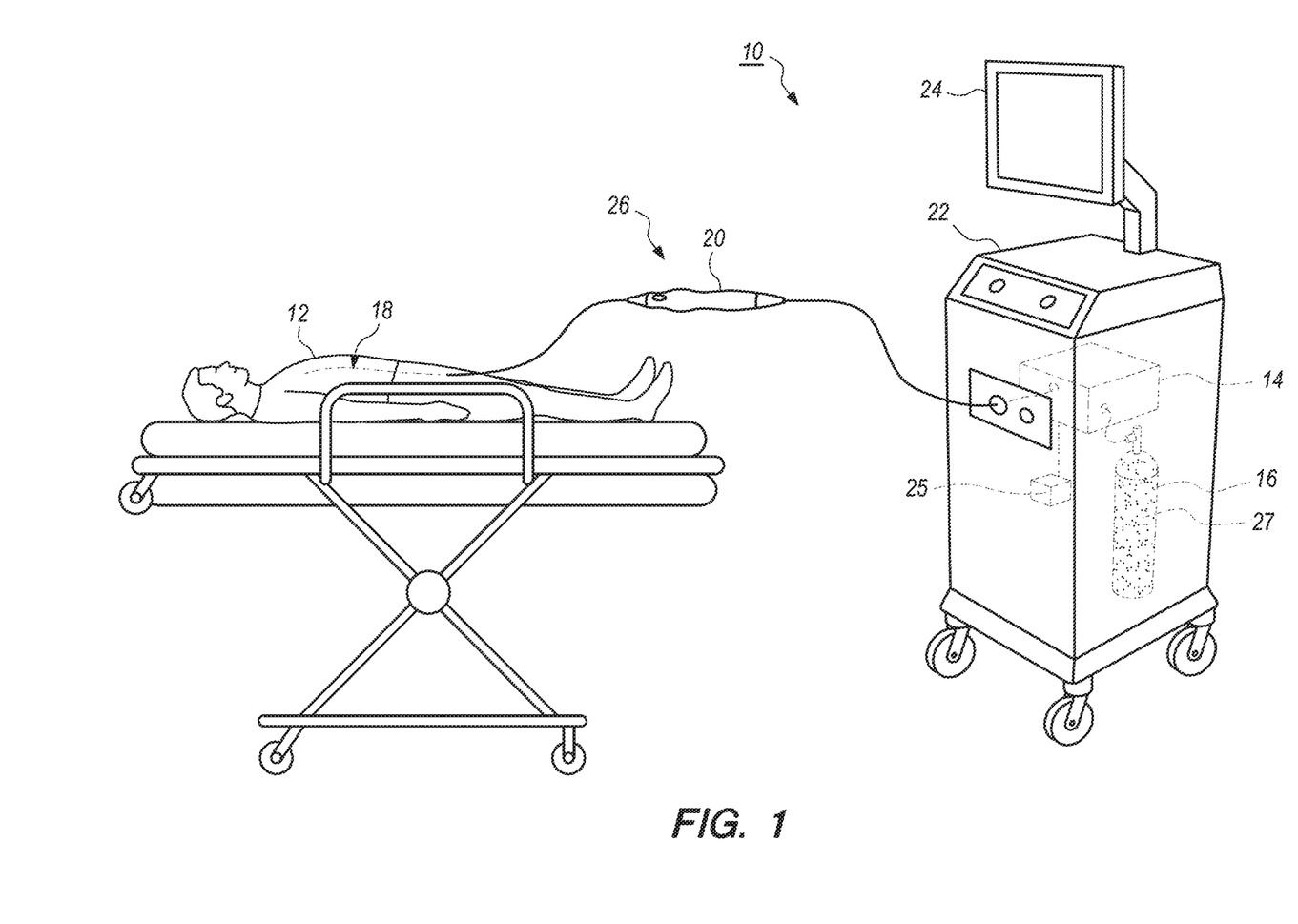
FIG. 1 is a schematic view of a patient and one embodiment of an intravascular catheter system having features of the present invention.

FIG. 1 is a schematic view of one embodiment of an intravascular catheter system 10 (also sometimes referred to as a "catheter system") for use with a patient 12, which can be a human being or an animal. Although the catheter system 10 is specifically described herein with respect to the intravascular catheter system, it is understood and appreciated that other types of catheter systems and/or ablation systems can equally benefit by the teachings provided herein. For example, in certain non-exclusive alternative embodiments, the present invention can be equally applicable for use with any suitable types of ablation systems and/or any suitable types of catheter systems. Thus, the specific reference herein to use as part of the intravascular catheter system is not intended to be limiting in any manner.

The design of the catheter system 10 can be varied. In certain embodiments, such as the embodiment illustrated in FIG. 1, the catheter system 10 can include one or more of a control system 14, a fluid source 16 (e.g., one or more fluid containers), a balloon catheter 18, a handle assembly 20, a control console 22, a graphical display 24 (also sometimes referred to as a graphical user interface or "GUI"), a vacuum pump 25 and a cryoballoon deflation assembly 26 (sometimes referred to herein as "deflation assembly"). It is understood that although FIG. 1 illustrates the structures of the catheter system 10 in a particular position, sequence and/or order, these structures can be located in any suitably different position, sequence and/or order than that illustrated in FIG. 1. It is also understood that the catheter system 10 can include fewer or additional structures than those specifically illustrated and described herein. For example, in one embodiment, the catheter system could include a foot control assembly (not shown), which can allow the operator to use his or her foot or feet to operate and/or control at least a portion of the cryoablation procedure.

In various embodiments, the control system 14 is configured to monitor and control the various processes of a cryoablation procedure. More specifically, the control system 14 can monitor and control release and/or retrieval of a cryogenic fluid 27 to and/or from the balloon catheter 18. The control system 14 can also control various structures that are responsible for maintaining or adjusting a flow rate and/or a pressure of the cryogenic fluid 27 that is released to the balloon catheter 18 during the cryoablation procedure. In such embodiments, the catheter system 10 delivers ablative energy in the form of cryogenic fluid 27 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive electrical signals, data and/or other information (also sometimes referred to as "sensor output") from various structures within the catheter system 10. In various embodiments, the control system 14, the GUI 24 and/or the deflation assembly 26 can be electrically connected and/or coupled. In some embodiments, the control system 14 can receive, monitor, assimilate and/or integrate any sensor output and/or any other data or information received from any structure within the catheter system 10 in order to control the operation of the balloon catheter 18. Still further, or in the alternative, the control system 14 can control positioning of portions of the balloon catheter 18 within the body of the patient 12, and/or can control any other suitable functions of the balloon catheter 18.

The fluid source 16 (also sometimes referred to as "fluid container 16") can include one or more fluid container(s) 16. It is understood that while one fluid container 16 is illustrated in FIG. 1, any suitable number of fluid containers 16 may be used. The fluid container(s) 16 can be of any suitable size, shape and/or design. The fluid container(s) 16 contains the cryogenic fluid 27, which is delivered to the balloon catheter 18 with or without input from the control system 14 during the cryoablation procedure. Once the cryoablation procedure has initiated, the cryogenic fluid 27 can be delivered and the resulting gas, after a phase change, can be retrieved from the balloon catheter 18, and can either be vented or otherwise discarded as exhaust (not shown). Additionally, the type of cryogenic fluid 27 that is used during the cryoablation procedure can vary. In one nonexclusive embodiment, the cryogenic fluid 27 can include liquid nitrous oxide. In another non-exclusive embodiment, the cryogenic fluid 27 can include liquid nitrogen. However, any other suitable cryogenic fluid 27 can be used.

The design of the balloon catheter 18 can be varied to suit the design requirements of the catheter system 10. As shown, the balloon catheter 18 is inserted into the body of the patient 12 during the cryoablation procedure. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a qualified healthcare professional (also referred to herein as an "operator"). As used herein, healthcare professional and/or operator can include a physician, a physician's assistant, a nurse and/or any other suitable person or individual. In certain embodiments, the balloon catheter 18 is positioned within the body of the patient 12 utilizing at least a portion of the sensor output that is received from the balloon catheter 18. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue. While specific reference is made herein to the balloon catheter 18, as noted above, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the catheter system 10. In the embodiment illustrated in FIG. 1, the handle assembly 20 is separate from, but in electrical and/or fluid communication with the control system 14, the fluid container 16 and the GUI 24. In some embodiments, the handle assembly 20 can integrate and/or include at least a portion of the control system 14 and/or deflation assembly 26 within an interior of the handle assembly 20. It is understood that the handle assembly 20 can include fewer or additional components than those specifically illustrated and described herein.

In the embodiment illustrated in FIG. 1, the control console 22 includes at least a portion of the control system 14, the fluid container 16, the GUI 24 and/or the deflation assembly 26. However, in alternative embodiments, the control console 22 can contain additional structures not shown or described herein. Still alternatively, the control console 22 may not include various structures that are illustrated within the control console 22 in FIG. 1. For example, in certain nonexclusive alternative embodiments, the control console 22 does not include the GUI 24.

In various embodiments, the GUI 24 is electrically connected to the control system 14. In some embodiments, the GUI may also be electrically connected to the deflation assembly 26. Additionally, the GUI 24 provides the operator of the catheter system 10 with information that can be used before, during and after the cryoablation procedure. For example, the GUI 24 can provide the operator with information based on the sensor output, and any other relevant information that can be used before, during and after the cryoablation procedure. The specifics of the GUI 24 can vary depending upon the design requirements of the catheter system 10, or the specific needs, specifications and/or desires of the operator.

In one embodiment, the GUI 24 can provide static visual data and/or information to the operator. In addition, or in the alternative, the GUI 24 can provide dynamic visual data and/or information to the operator, such as video data or any other data that changes over time, e.g., during the cryoablation procedure. Further, in various embodiments, the GUI 24 can include one or more colors, different sizes, varying brightness, etc., that may act as alerts to the operator. Additionally, or in the alternative, the GUI 24 can provide audio data or information to the operator.

The vacuum pump 25 can remove, evacuate or retrieve some or substantially all of the cryogenic fluid 27 from within the balloon catheter 18. The design and specific features of the vacuum pump 25 can vary. In the embodiment illustrated in FIG. 1, the vacuum pump 25 is separate from, but in electrical and/or fluid communication with the control system 14, the balloon catheter 18, the handle assembly 20 and/or the deflation assembly 26. As referred to herein, when the vacuum pump 25 is activated, the vacuum pump 25 is pulling a vacuum and actively removing, evacuating or retrieving some or substantially all of the cryogenic fluid 27 from within the balloon catheter 18. During cryoablation procedures, the vacuum pump 25 can be activated to remove, evacuate or retrieve some of the cryogenic fluid 27 from the balloon catheter 18, for example, to maintain an appropriate balloon pressure within the balloon catheter 18. Upon completion of any stage of the cryoablation procedure, the vacuum pump 25 can be activated to remove, evacuate or retrieve substantially all of the cryogenic fluid 27 from within the balloon catheter 18 to allow the balloon catheter 18 to be more safely removed from the patient 12. In contrast, in certain embodiments, the vacuum pump 25 may not be activated. As used herein, the vacuum pump 25 is not activated when it is not actively removing, evacuating or retrieving some and/or substantially all of the cryogenic fluid 27 from the balloon catheter 18 during the cryoablation procedure and/or upon completion of the cryoablation procedure.

As an overview, and as provided in greater detail herein, at an appropriate time the deflation assembly 26 can be configured to initiate elongation of a portion of the balloon catheter 18. Additionally, or in the alternative, the deflation assembly 26 can be configured to initiate and/or activate the vacuum pump 25 to remove some and/or substantially all of the cryogenic fluid 27 from within the balloon catheter 18. For example, during the cryoablation procedure and/or upon completion of the cryoablation procedure, the deflation assembly 26 can automatically elongate a portion of the balloon catheter 18. Thereafter, and/or simultaneously, the deflation assembly 26 can automatically initiate removal of substantially all of the cryogenic fluid 27 from within the balloon catheter 18. In another embodiment, the deflation assembly 26 can be configured to allow the operator to manually and/or selectively elongate a portion of the balloon catheter 18 and/or initiate removal of substantially all of the cryogenic fluid 27 from within the balloon catheter 18. In one embodiment, the deflation assembly 26 can include the vacuum pump 25. Alternatively, in another embodiment, the vacuum pump 25 is not included in the deflation assembly 26.

In the embodiment illustrated in FIG. 1, at least a portion of the deflation assembly 26 is integrated with the handle assembly 20. The deflation assembly 26 can be positioned at any suitable location within the handle assembly 20. Further, portions of the deflation assembly 26 can be positioned partially within and/or outside the handle assembly 20. Alternatively, at least a portion of the deflation assembly 26 can be integrated with the GUI 24. The deflation assembly 26 can be integrated with the GUI 24 via any suitable manner or method. Still alternatively, at least a portion of the deflation assembly 26 can be positioned at any suitable location within and/or outside the control console 22. Additionally, and/or alternatively, the deflation assembly 26 can be positioned at any other suitable location within the catheter system 10. In various embodiments, at least a portion of the deflation assembly 26 can be electrically connected and/or coupled to the control system 14 and/or the GUI 24.

Figure 2A:
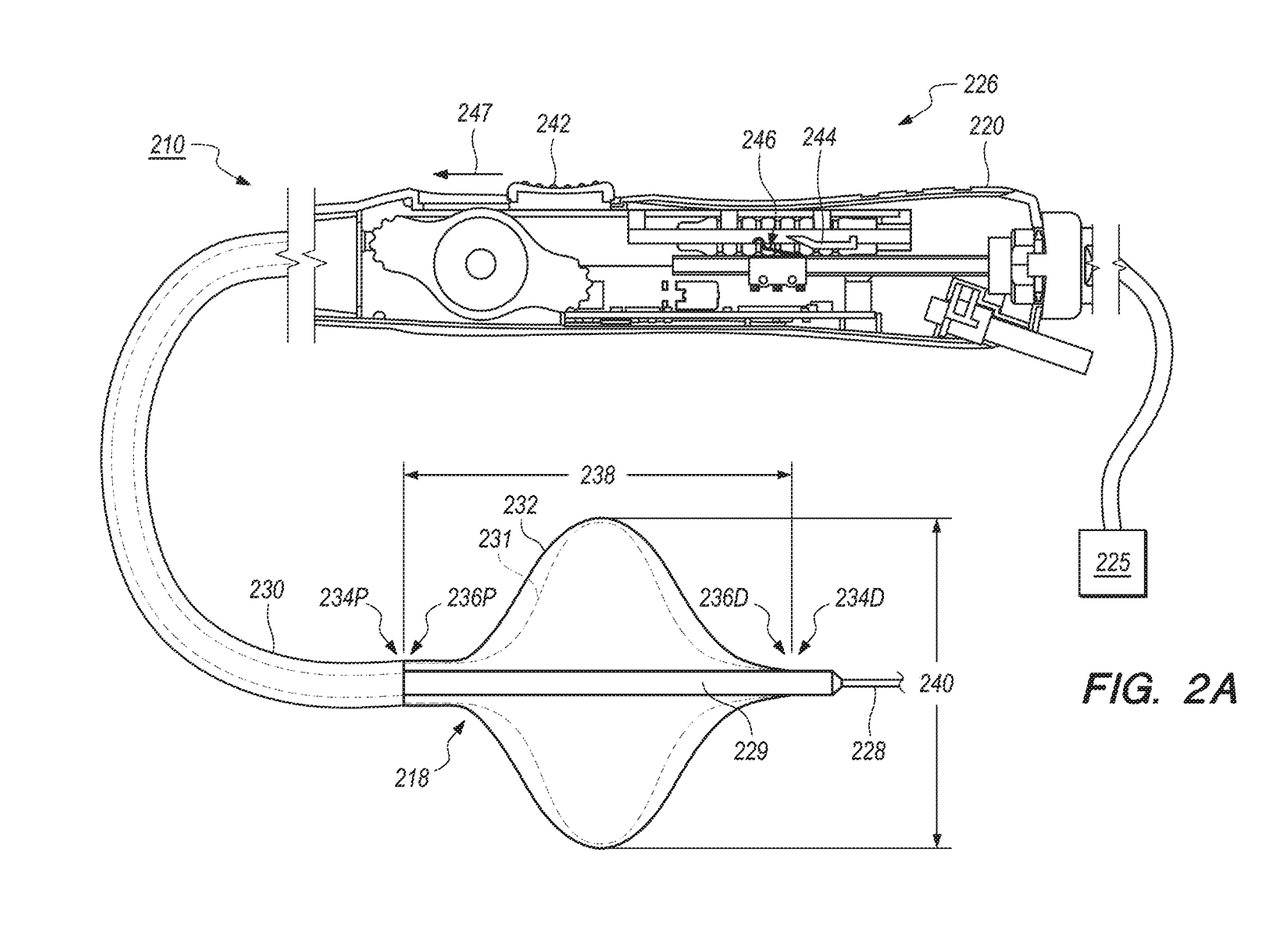
FIG. 2A is a partial cutaway view of a balloon catheter in an inflated state and an embodiment of a portion of the intravascular catheter system including one embodiment of a cryoballoon deflation assembly.

FIG. 2A is a simplified, partial cutaway view of one embodiment of a portion of the catheter system 210. In this embodiment, the catheter system 210 includes the balloon catheter 218 illustrated in an inflated state, the handle assembly 220, the vacuum pump 225 and one embodiment of the deflation assembly 226. It is understood that the structures illustrated in FIG. 2A are not necessarily shown to scale. [0047] In the embodiment illustrated in FIG. 2A, the balloon catheter 218 includes one or more of a guidewire 228, guidewire lumen 229, a catheter shaft 230, an inner cryoballoon 231 and an outer cryoballoon 232. It is recognized that the inner cryoballoon 231 and the outer cryoballoon 232 can also be referred to as a "first cryoballoon" and a "second cryoballoon", and that either cryoballoon 231, 232 can be the first cryoballoon or the second cryoballoon. It is also understood that the balloon catheter 218 can include other structures as well. However, for clarity these other structures have been omitted from FIG. 2A.

The guidewire 228 can be inserted near and/or into a pulmonary vein (not shown) of the patient 12 (illustrated in FIG. 1), and the guidewire lumen 229, catheter shaft 230 and the cryoballoons 231, 232 can be moved along the guidewire lumen 228 to near an ostium (not shown) of the pulmonary vein.

In various embodiments, the inner cryoballoon 231 includes a proximal inner cryoballoon region 234P and a distal inner cryoballoon region 234D. As referenced herein, "proximal" means a location on the cryoballoons 231, 232 that is closer to the handle assembly 220, while "distal" means a location on the cryoballoons 231, 232 that is further away or more distant from the handle assembly 220. In one embodiment, the proximal inner cryoballoon region 234P can be secured or attached to the catheter shaft 230. Further, the distal inner cryoballoon region 234D can be secured or attached to the guidewire lumen 229. Alternatively, the proximal inner cryoballoon region 234P and/or the distal inner cryoballoon region 234D can be secured or attached to other suitable structures within the catheter system 210. The proximal inner cryoballoon region 234P and/or the distal inner cryoballoon region 234D can be secured or attached to the guidewire lumen 229, the catheter shaft 230 and/or any other suitable structures, via any manner or method, such as with an adhesive or bonding material, as non-exclusive examples In certain embodiments, the outer cryoballoon 232 includes a proximal outer cryoballoon region 236P and a distal outer cryoballoon region 236D. In one embodiment, the proximal outer cryoballoon region 236P can be secured or attached to the catheter shaft 230. Further, the distal outer cryoballoon region 236D can be secured or attached to the guidewire lumen 229. Alternatively, the proximal outer cryoballoon region 236P and/or the distal outer cryoballoon region 236D can be secured to other suitable structures within the catheter system 210. The proximal outer cryoballoon region 236P and/or the distal outer cryoballoon region 236D can be secured or attached to the guidewire lumen 229, the catheter shaft 230 and/or any other suitable structures, via any manner or method, such as with an adhesive or bonding material, as non-exclusive examples.

During the cryoablation procedure, the inner cryoballoon 231 can be partially or fully inflated so that at least a portion of the inner cryoballoon 231 expands against a portion of the outer cryoballoon 232. As provided herein, once the inner cryoballoon 231 is sufficiently inflated, the outer cryoballoon 232 can then be properly positioned within the patient 12 to abut and/or form a seal with the relevant portion(s) of the circulatory system (not shown) of the patient 12, such as the ostium of the pulmonary vein, for example.

In certain embodiments, the balloon catheter 218 can be in the inflated state or a deflated state. When the balloon catheter 218 is in the inflated state, as shown in FIG. 2A, the vacuum pump 225 is not actively deflating one or more cryoballoons 231, 232. As referred to herein, "deflate" means to remove substantially all of the cryogenic fluid 27 (illustrated in FIG. 1) from one or more cryoballoons 231, 232. In other words, when the balloon catheter 218 is in the inflated state, the vacuum pump 225 can be actively removing some, but not substantially all, of the cryogenic fluid 27 from the one or more cryoballoons 231, 232. Additionally, when the balloon catheter 218 is in the inflated state, the outer cryoballoon 232 has an inflated outer cryoballoon length 238 and an inflated outer cryoballoon width 240.

Additionally, during the cryoablation procedure, the cryogenic fluid 27 being injected into the one or more cryoballoons 231, 232 can include an injection flow rate. As used herein, the injection flow rate includes a flow rate of the cryogenic fluid 27 being injected into the balloon catheter 218. Alternatively, the cryogenic fluid 27 being removed from the one or more cryoballoons 231, 232 can include an exhaust flow rate. As used herein, the exhaust flow rate includes a flow rate of the cryogenic fluid 27 being removed from the balloon catheter 218. In one embodiment, the inflated state can also include the injection flow rate that is substantially the same as the exhaust flow rate. Alternatively, the inflated state can include any injection flow rate and/or exhaust flow rate sufficient to maintain the cryoballoons 231, 232 from falling out of position.

Conversely, when in the balloon catheter 218 is in the deflated state (illustrated in FIG. 2B), the vacuum pump 225 is actively deflating one or more cryoballoons 231, 232. In other words, when the balloon catheter 218 is in the deflated state, the vacuum pump 225 can be actively removing substantially all of the cryogenic fluid 27 from the one or more cryoballoons 231, 232. The deflated state may also include reducing the injection flow rate while maintaining the exhaust flow rate constant and/or increasing the exhaust flow rate while maintaining the injection flow rate constant.

The handle assembly 220 is used by the operator to control various functions of the balloon catheter 218 and/or the deflation assembly 226. In the embodiment illustrated in FIG. 2A, the handle assembly 220 includes at least a portion of the deflation assembly 226. Alternatively, the deflation assembly 226 can be positioned remotely from the handle assembly 220, such as on or within the control console 22 or GUI 24 (illustrated in FIG. 1), for example.

Additionally, as referred to herein, each cryoablation procedure can include various stages, which may include: (i) the inflation stage, (ii) ablation stage, and (iii) thawing stage, as non-exclusive examples. As utilized herein, "inflation stage" refers generally to the stage of the cryoablation procedure prior to the ablation stage, wherein the cryogenic fluid 27 is delivered from the fluid container 16 (illustrated in FIG. 1) to the cryoballoons 231, 232 at the injection flow rate that does not cause tissue necrosis. During inflation of the cryoballoons 231, 232, the operator may adjust or position the cryoballoons 231, 232 within the body of the patient 12 to achieve positioning of the cryoballoons 231, 232 adjacent to the targeted tissue of the patient 12. The targeted tissue includes at least a portion of heart tissue of the patient 12 that is to be treated by the catheter system 210, such as the pulmonary vein, for example. Once positioned adjacent to targeted tissue and the pulmonary vein is occluded, ablation of the targeted tissue may be initiated.

The "ablation stage" refers generally to the stage of the cryoablation procedure when the cryogenic fluid 27 is delivered from the fluid container 16 to the cryoballoons 231, 232 at the injection flow rate to create tissue necrosis. Tissue necrosis has the effect of rendering targeted tissue incapable of conducting cardiac electrical signals. During ablation of the targeted tissue, the cryoballoons 231, 232 are positioned adjacent to targeted tissue, with the pulmonary vein being occluded.

The "thawing stage" refers generally to the stage of the cryoablation procedure when the cryogenic fluid 27 is delivered from the fluid container 16 to the cryoballoons 231, 232 with the injection flow rate and/or the exhaust flow rate sufficient to maintain the cryoballoons 231, 232 partially or substantially inflated to inhibit the balloon catheter 218, including the cryoballoons 231, 232, from falling out of position and/or to reduce the likelihood of tissue damage to the patient 12. Accordingly, thawing can include removing some, but not substantially all, of the cryogenic fluid 27 from the balloon catheter 218. Thawing can be temperature based, time based, or both. Temperature based means that the ablated heart tissue is allowed to thaw to a certain temperature. Time based means the ablated heart tissue is allowed to thaw for a certain period of time. The temperature and period of time can vary depending on the patient 12 and/or any other cryoablation parameters. Additionally, and/or alternatively, it is understood that the cryoablation procedure may also include other stages not specifically mentioned herein.

In various embodiments, the deflation assembly 226 can initiate elongation of the guidewire lumen 229, including the inner cryoballoon 231 and/or the outer cryoballoon 232 which can be at least partially secured or attached to the guidewire lumen 229, as well as initiating deflation, i.e., removal of substantially all of the cryogenic fluid 27 from one or more of the cryoballoons 231, 232, via the vacuum pump 225. In one embodiment, the deflation assembly 226 can be configured to automatically initiate the elongation of the guidewire lumen 229 upon termination of any stage of the cryoablation procedure, such as the inflation stage, ablation stage and/or thawing stage. Alternatively, the deflation assembly 226 can be configured to allow the operator to manually or selectively initiate elongation of the guidewire lumen 229 via any suitable manner or method, such as with the use of one or more switches, levers or buttons, for example.

Additionally, in some embodiments, the deflation assembly 226 can be configured to automatically initiate deflation of one or more of the cryoballoons 231, 232, via the vacuum pump 225, upon termination of any stage of the cryoablation procedure. In other embodiments, the deflation assembly 226 can be configured to sense when the guidewire lumen 229 has been elongated to initiate deflation of one or more of the cryoballoons 231, 232. In alternative embodiments, the deflation assembly 226 can be configured to allow the operator to manually or selectively initiate deflation of one or more of the cryoballoons 231, 232, via any suitable manner or method, which may include the use of one or more switches, levers or buttons, as non-exclusive examples.

Furthermore, in certain embodiments, the deflation assembly 226 can be configured to automatically reduce the injection flow rate upon termination of any stage of the cryoablation procedure. The deflation assembly 226 can also be configured to automatically increase the injection flow rate and/or increase or decrease the exhaust flow rate. In alternative embodiments, the deflation assembly 226 can be configured to allow the operator to manually or selectively reduce the injection flow rate, via any suitable manner or method, which may include the use of one or more switches, levers or buttons, as non-exclusive examples. The deflation assembly 226 can also be configured to allow the operator to manually or selectively increase the injection flow rate and/or increase or decrease the exhaust flow rate.

The specific design of the deflation assembly 226 can vary to suit the design requirements of the catheter system 210. In the embodiment illustrated in FIG. 2A, the deflation assembly 226 includes one or more of an initiator 242, a switch activator 244 and a switch 246.

In FIG. 2A, the initiator 242 moves the switch activator 244 to activate the switch 246. In certain embodiments, the initiator 242 can mechanically or electrically cause elongation or extension of the guidewire lumen 229 in a direction away from the handle assembly 220. In other embodiments, the initiator 242 can initiate deflation of one or more cryoballoons 231, 232, via the vacuum pump 225. In one embodiment, the initiator 242 can include a slidable element that can be slid (or otherwise moved) by the operator in a general direction toward the balloon catheter 218, shown by arrow 247, in order to elongate or extend the guidewire lumen 229, including the inner cryoballoon 231 and/or the outer cryoballoon 232 which can be partially secured or attached to the guidewire lumen 229, and/or to initiate deflation of one or more cryoballoons 231, 232. In another embodiment, the initiator 242 can include a plurality of buttons, with each button corresponding to elongation or deflation, such that alternatingly depressing each of the buttons selectively causes either elongation of the guidewire lumen 229 and/or deflation of one or more cryoballoons 231,

232. In still other embodiments, the initiator 242 can include one or more lever(s) or switch(es) that can be selectively and/or manually moved to enable the operator to selectively and/or manually cause elongation of the guidewire lumen 229 and/or deflation of one or more cryoballoons 231, 232. Alternatively, the initiator 242 can have any other suitable design that effectively enables the operator to selectively and/or manually actuate the initiator 242 to cause the elongation of the guidewire lumen 229 and/or the deflation of one or more cryoballoons 231, 232.

In an alternative embodiment, the initiator 242 can include a push button or any other suitable type of device that moves the switch activator 244 and extends the guidewire lumen 229 in a direction away from the handle assembly 220 and/or initiates deflation of one or more cryoballoons 231, 232. For example, the initiator 242 can include the push button wherein elongation and/or deflation of one or more cryoballoons 231, 232 can be initiated depending on the number of times the operator depresses the push button. More specifically, in certain embodiments, when the initiator 242 has been actuated and/or depressed a first time, the initiator 242 can send electrical signals, data or other information, to cause elongation of the guidewire lumen 229. In the event the initiator 242 has been actuated and/or depressed a second time, the initiator 242 can send electrical signals, data or other information, to initiate deflation of one or more cryoballoons 231, 232.

In various embodiments, the initiator 242 can be slid or moved into a plurality of different positions, i.e., a first position and a second position. Depending on the position of the initiator 242, the initiator 242 can send electrical signals, data or other information, to cause elongation of the guidewire lumen 229 and/or deflation of one or more cryoballoons 231, 232. For example, the initiator 242 can include the slidable element, switch or lever, wherein elongation and/or deflation of one or more cryoballoons 231, 232 can be initiated depending on the positioning of the slidable element, switch or lever. More specifically, in certain embodiments, when the initiator 242 has been positioned in a first position, the initiator 242 can send electrical signals, data or other information, to cause elongation of the guidewire lumen 229. In the event the initiator 242 has been positioned in a second position, the initiator 242 can send electrical signals, data or other information, to initiate deflation of one or more cryoballoons 231, 232.

In other embodiments, such as the embodiment illustrated in FIG. 2A, when the initiator 242 is in the first position, i.e., or a retracted position, the switch activator 244 does not activate the switch 246. With the switch 246 not activated, the cryoballoons 231, 232, are not being actively elongated and/or deflated. In one embodiment, the switch activator 244 can be part of the initiator 242 so that movement of the initiator 242 directly activates and/or deactivates the switch 246.

In one embodiment, the deflation assembly 226 can include the vacuum pump 225. In such embodiment, the deflation assembly 226 can initiate deflation of one or more of the cryoballoons 231, 232, via the vacuum pump 225, upon termination of any stage of the cryoablation procedure, such as the inflation stage, the ablation stage and/or the thawing stage. It is understood, however, that the vacuum pump 225 (or a different vacuum pump designated for such purpose) can be used intermittently during the cryoablation procedure to remove some of the cryogenic fluid 27 from one or more cryoballoons 231, 232, for example, to maintain an appropriate balloon pressure within the one or more cryoballoons 231, 232.

Figure 2B:
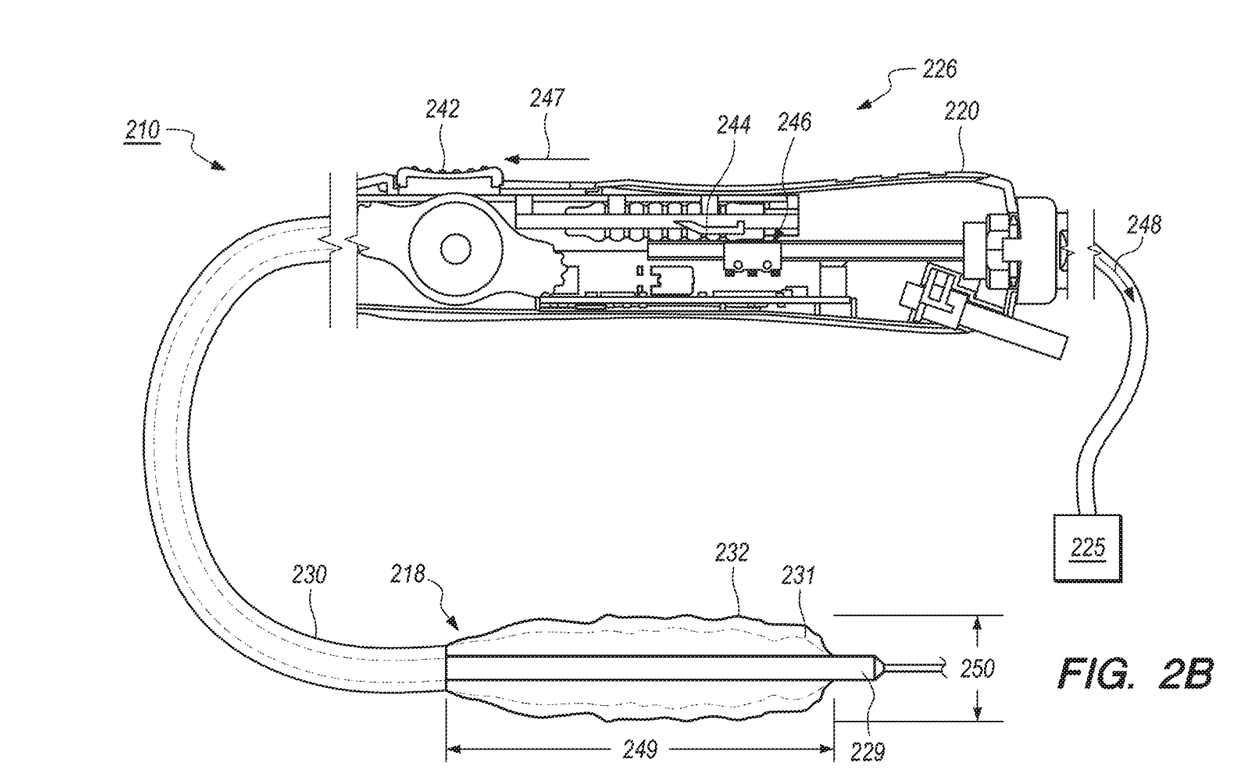
FIG. 2B is a partial cutaway view of the balloon catheter in a deflated state and the portion of the intravascular catheter system illustrated in FIG. 2A, including the cryoballoon deflation assembly.

FIG. 2B is a simplified, partial cutaway view of the portion of the catheter system 210 illustrated in FIG. 2A. In this embodiment, the catheter system 210 includes the balloon catheter 218 illustrated in the deflated state, the handle assembly 220, the vacuum pump 225 and the deflation assembly 226. Again, the structures illustrated in FIG. 2B are not necessarily shown to scale.

In FIG. 2B, the initiator 242 is illustrated to have been moved in a direction shown by arrow 247. This movement causes the switch activator 244 to activate the switch 246. In addition, when the initiator 242 is moved in the direction of arrow 247, elongation or extension of the guidewire lumen 229 in a direction away from the handle assembly 220, i.e., in the direction of arrow 247, occurs in order to elongate the guidewire lumen 229, including the inner cryoballoon 231 and/or the outer cryoballoon 232 which can be at least partially secured and/or attached to the guidewire lumen 229.

In the embodiment illustrated in FIG. 2B, the second position, i.e., or activated position, can cause the switch activator 244 to contact and/or otherwise activate the switch 246. With the switch 246 activated, the vacuum pump 225 operates to pull a vacuum in the direction of arrow 248 within one or more of the cryoballoons 231, 232, to deflate, i.e., remove substantially all of the cryogenic fluid 27 (illustrated in FIG. 1), from the one or more cryoballoons 231, 232. It is understood that the activation of the switch, and deflation of one or more cryoballoons 231, 232, via the vacuum pump 225, can occur either sequentially (in either order) or substantially simultaneously.

When the balloon catheter 218 is in the deflated state, the vacuum pump 225 is actively removing most or substantially all of the cryogenic fluid 27 from one or more cryoballoons 231, 232. Additionally, when the balloon catheter 218 is in the deflated state, the outer cryoballoon 232 has a deflated outer cryoballoon length 249 that is greater than the inflated outer cryoballoon length 238 (illustrated in FIG. 2A). Further, when the balloon catheter 218 is in the deflated state, the outer cryoballoon 232 has a deflated outer cryoballoon width 250 that is less than the inflated outer cryoballoon width 240 (illustrated in FIG. 2A). Such a configuration allows the cryoballoons 231, 232 to more fully achieve a minimum profile, which allows the cryoballoons 231, 232 to be more effectively retracted into the catheter shaft 230.

Once the cryoballoons 231, 232 have been elongated and a sufficient amount of the cryogenic fluid 27 has been removed from one or more cryoballoons 231, 232 using the deflation assembly 226, the guidewire lumen 229 can be retracted in a direction toward the handle assembly 220, i.e., in the direction opposite of arrow 247, so that the balloon catheter 218 can safely be removed from the patient 12 (illustrated in FIG. 1).

Figure 3A:
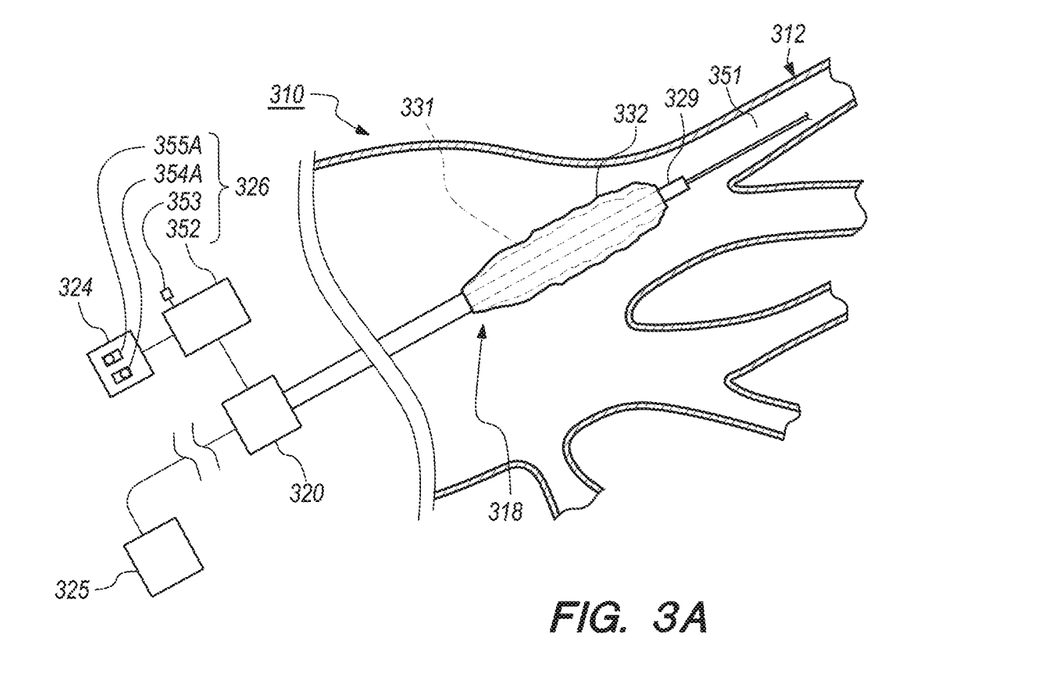
FIG. 3A is a simplified side view of a portion of the patient and still another embodiment of a portion of the intravascular catheter system including another embodiment of the cryoballoon deflation assembly.

FIG. 3A is a simplified side view of a portion of the patient 312 and still another embodiment of a portion of the catheter system 310 including another embodiment of the deflation assembly 326. In the embodiment illustrated in FIG. 3A, the catheter system 310 can include one or more of the balloon catheter 318, the handle assembly 320, the GUI 324, the vacuum pump 325 and the deflation assembly 326.

In this embodiment, the balloon catheter 318 includes the inner cryoballoon 331 and the outer cryoballoon 332. During the cryoablation procedure, the cryoballoons 331, 332 can be partially or fully inflated so that at least a portion of the inner cryoballoon 331 expands toward and/or against a portion of the outer cryoballoon 332 (although a space is shown between the inner cryoballoon 331 and the outer cryoballoon 332 in FIG. 3A for clarity). When the cryoballoons 331, 332 are partially or fully inflated, the cryoballoons 331, 332 can be positioned within the patient 312 to perform the cryoablation procedure after occluding blood flow from the pulmonary vein 351 of the patient 312. Alternatively, the cryoballoons 331, 332 can be partially or fully deflated at any point during the cryoablation procedure and/or upon termination of any stage of the cryoablation procedure, which can include the inflation stage, the ablation stage and/or the thawing stage, as non-exclusive examples.

Once treated, diseased heart tissue can be allowed to thaw to a certain temperature and/or for a certain period of time. In other words, upon completion of the ablation stage, the thawing stage can be initiated. During the thawing stage, the cryoballoons 331, 332 can remain partially and/or fully inflated to maintain the positioning of the cryoballoons 331, 332 and/or to help prevent tissue damage to the patient 312. In other words, the balloon catheter 318 can be maintained in the inflated state during the thawing stage.

The GUI 324 allows the operator to interact with the catheter system 310. In various embodiments, the GUI 324 can include, be integrated with and/or electrically connected to at least a portion of the deflation assembly 326. In such embodiments, the operator can manipulate the GUI 324, which can be configured to allow the operator to selectively trigger and/or initiate (i) elongation of the guidewire lumen 329, (ii) deflation of one or more cryoballoons 331, 332 via the vacuum pump 325 and/or (iii) reduction of the injection flow rate. In the embodiment illustrated in FIG. 3A, at least a portion of deflation assembly 326 can be at least partially integrated with and/or positioned on the GUI 324. Although this embodiment relates to deflation of one or more cryoballoons 331, 332 via the vacuum pump 325, it is understood that the embodiment can equally apply or relate to the elongation of the guidewire lumen 329 and/or reduction of the injection flow rate.

In certain embodiments, the vacuum pump 325 can be activated upon termination of any stage of the cryoablation procedure to deflate one or more cryoballoons 331, 332. In other embodiments, the vacuum pump 325 can be activated at any time or stage during the cryoablation procedure to remove some of the cryogenic fluid 27 (illustrated in FIG. 1) from one or more cryoballoons 331, 332, for example, to maintain an appropriate cryoballoon pressure within the one or more cryoballoons 331, 332 during thawing.

The design and specific features of the deflation assembly 326 can vary to suit the design requirements of the catheter system 310. In the embodiment illustrated in FIG. 3A, the deflation assembly 326 can be configured to initiate deflation of one or more cryoballoons 331, 332 via the vacuum pump 325. The deflation assembly 326 can include a controller 352, a first deflation initiator 353, a first deflation initiator inhibitor 354A and a second deflation initiator 355A. It is understood that the deflation assembly 326 can include fewer or additional components than those specifically illustrated and described herein. For example, in certain non-exclusive embodiments, the deflation assembly 326 does not include the controller 352.

In various embodiments, the controller 352 is configured to receive electronic or other signals from the first deflation initiator inhibitor 354A and/or second deflation initiator 355A. The design of the controller 352 can vary. Further, in certain embodiments, the control system 14 (illustrated in FIG. 1) can integrate and/or include the controller 352. However, in this embodiment, the controller 352 is separate from the control system 14. Additionally, and/or alternatively, the controller 352 can be integrated and/or included as part of any other suitable component or structure of the catheter system 310.

The design of the first deflation initiator 353 can vary. The first deflation initiator 353 can be configured to automatically activate the vacuum pump 325 to deflate the one or more cryoballoons 331, 332 upon completion of at least one stage of the cryoablation procedure, which can include the inflation stage, the ablation stage and/or the thawing stage, as non-exclusive examples. In other words, the first deflation initiator 353 can automatically initiate removal of substantially all of the cryogenic fluid 27 (illustrated in FIG. 1) from within the balloon catheter 318. The first deflation initiator 353 can automatically initiate deflation of the one or more cryoballoons via any suitable manner or method. Additionally, the first deflation initiator can be connected to, integrated with and/or positioned on any suitable component or structure of the catheter system 310. In the embodiment illustrated in FIG. 3A, the first deflation initiator 353 is separate from, but electrically connected with the controller 352, for example.

As described herein, the first deflation initiator inhibitor 354A can be selectively and/or manually changeable between an activated state and a deactivated state. When in the activated state, the first deflation initiator inhibitor 354A can be configured to inactivate the first deflation initiator 353. In other words, when the first deflation initiator is inactivated, i.e., the vacuum pump 325 will not automatically deflate the cryoballoons 331, 332 upon termination of any stage of the cryoablation procedure. The first deflation initiator inhibitor 354A can inactivate the first deflation initiator 353 via any suitable manner or method, such as mechanically or electrically, as non-exclusive examples. In one non-exclusive embodiment, when in the activated state, the first deflation initiator inhibitor 354A can be configured to send a first signal to the controller 352. The controller 352 can receive and process the first signal to inactivate the first deflation initiator 353. Furthermore, when the first deflation initiator inhibitor 354A is in the activated state, as shown in FIG. 3A, the operator can then manually or selectively initiate deflation of one or more cryoballoons 331, 332 via the vacuum pump 325 with the use of additional switches, levers, buttons, slidable members, etc., such as the second deflation initiator 355A, for example. The additional switches, levers, buttons, slidable members, etc., including the second deflation initiator 355A, referred to herein, can be positioned and/or integrated on any suitable structure of the catheter system 310, such as the GUI 324, for example.

The function and/or design of the first deflation initiator inhibitor 354A can vary. In the embodiment illustrated in FIG. 3A, the first deflation initiator inhibitor 354A includes a switch located on the GUI 324. In this embodiment, the switch is shown toggled to the right, which is the activated state. In alternative embodiments, in order to activate the switch, it can be moved in different directions, such as to the left. Further, in this embodiment, the first deflation initiator inhibitor 354A can move between a first position and a second position. In other embodiments, the first deflation initiator inhibitor 354A can move between any number of positions, i.e., first position, second position, third position, etc. In such embodiments, only one of the positions of the first deflation initiator inhibitor 354A can inactivate the first deflation initiator 353 and/or trigger the second deflation initiator 355A.

In another embodiment, the first deflation initiator inhibitor 354A can include a touch screen. In still another embodiment, the first deflation initiator inhibitor 354A can include a maneuverable dial. In yet another embodiment, the first deflation initiator inhibitor 354A can include voice activation. Still, the first deflation initiator inhibitor 354A can also include any other suitable design, such as a control button or lever, as non-exclusive examples. The first deflation initiator inhibitor 354A can be positioned, integrated and/or included as part of the handle assembly 320 or the control console 322. Alternatively, the first deflation initiator inhibitor 354A can be positioned, integrated and/or included as part of any suitable structure and/or component within the catheter system 310, including the foot control assembly (not shown), for example.

The second deflation initiator 355A can also be configured to be selectively and/or manually changeable between an activated state and a deactivated state. In certain embodiments, the second deflation initiator 355A is triggered when the first deflation initiator inhibitor 354A is in the activated state. In this embodiment, the second deflation initiator 355A is shown in the activated state. The second deflation initiator 355A can be triggered via any suitable manner or method, such as mechanically or electrically, as non-exclusive examples. In one non-exclusive embodiment, when in the activated state, the second deflation initiator 355A can be configured to send a second signal to the controller 352. The controller 352 can receive and process the second signal to active the vacuum pump 325 to deflate the one or more cryoballoons 331, 332. Alternatively, when in the deactivated state, the vacuum pump 325 is not activated to deflate the one or more cryoballoons 331, 332. However, although not activated to deflate the one or more cryoballoons 331, 332, the vacuum pump 325 may still be activated to remove some, but not substantially all, of the cryogenic fluid 27 from the one or more cryoballoons 331, 332.

The function and/or design of the second deflation initiator 355A can vary. In the embodiment illustrated in FIG. 3A, the second deflation initiator 355A includes a switch located on the GUI 324. In this embodiment, the switch is shown toggled to the left, which is the activated state. In alternative embodiments, in order to activate the switch, it can be moved in different directions, such as to the right. Further, in this embodiment, the second deflation initiator 355A can move between a first position and a second position. In other embodiments, the second deflation initiator 355A can move between any number of positions, i.e., first position, second position, third position, etc. In such embodiments, only one of the positions of the second deflation initiator 355A can activate the vacuum pump 325 to deflate the one more cryoballoons 331, 332. Alternatively, the second deflation initiator 355A can include any other suitable design, such as a control button, lever or dial, as nonexclusive examples.

Figure 3B:
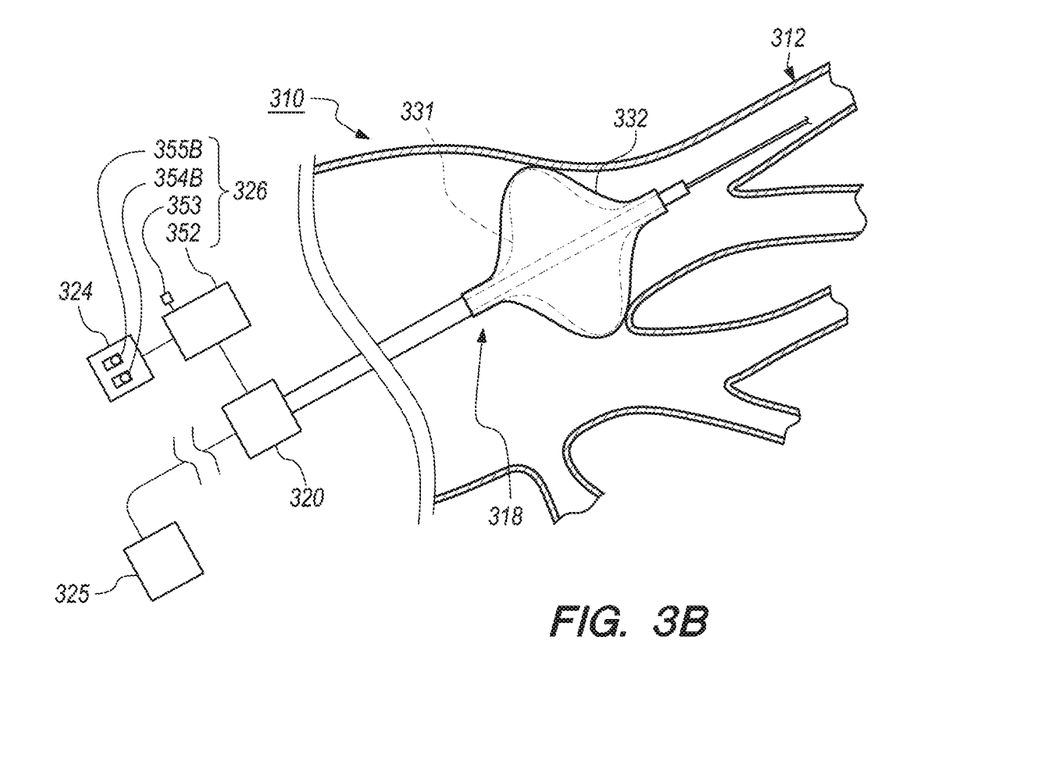
FIG. 3B is a simplified side view of a portion of the patient and yet another embodiment of a portion of the intravascular catheter system including still another embodiment of the cryoballoon deflation assembly.

FIG. 3B is a simplified side view of a portion of the patient 312 and yet another embodiment of a portion of the catheter system 310 including still another embodiment of the deflation assembly 326. In the embodiment illustrated in FIG. 3B, the catheter system 310 includes the balloon catheter 318, the handle assembly 320, the GUI 324, the vacuum pump 325 and the deflation assembly 326.

In the embodiment illustrated in FIG. 3B, the first deflation initiator inhibitor 354B is in the activated state, with the switch toggled to the right. As such, the second deflation initiator 355B has been triggered and the first deflation initiator 353 has been inactivated. However, in this embodiment, the second deflation initiator 355B is the deactivated state, with the switch toggled to the right. When in the deactivated state, the vacuum pump 325 has not been activated to initiate deflation, i.e., removal of substantially all of the cryogenic fluid 27 (illustrated in FIG. 1), from the cryoballoons 331, 332. In other words, the vacuum pump 325 can remove some, but not substantially all of the cryogenic fluid 27, in order to maintain the cryoballoons 331, 332 partially or substantially inflated to inhibit the balloon catheter 318 from falling out of position and/or to reduce the likelihood of tissue damage to the patient 312.

Figure 3C:
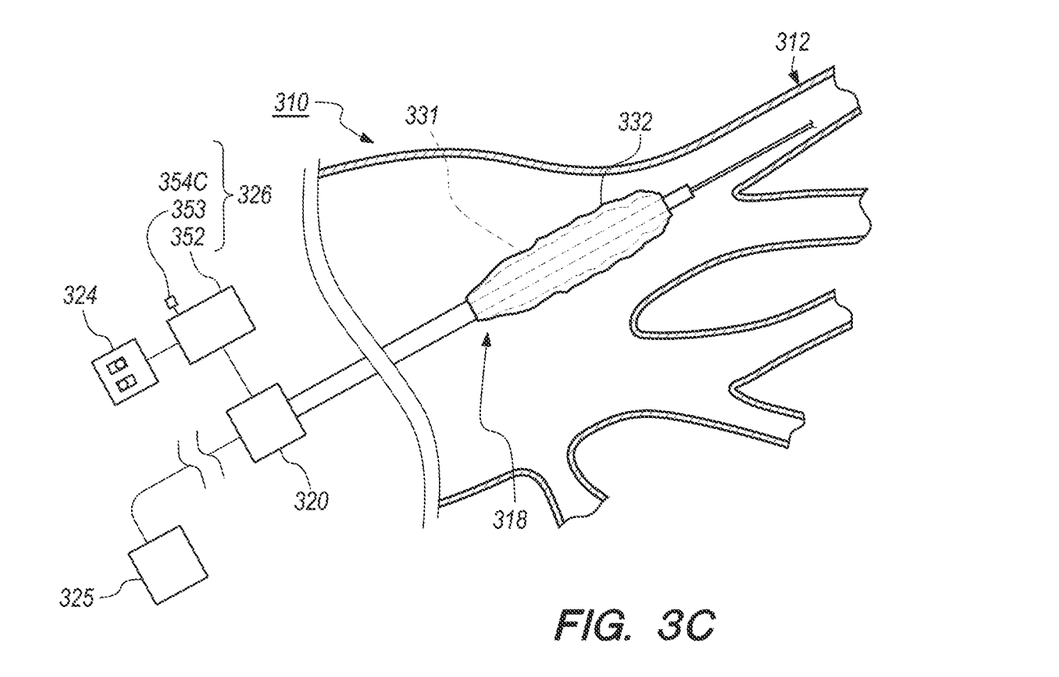
FIG. 3C is a simplified side view of the portion of the patient and a portion of even another embodiment of the intravascular catheter system including yet another embodiment of the cryoballoon deflation assembly.

FIG. 3C is a simplified side view of the portion of the patient 312 and a portion of even another embodiment of the catheter system 310 including yet another embodiment of the deflation assembly 326. In the embodiment illustrated in FIG. 3C, the catheter system 310 includes the balloon catheter 318, the handle assembly 320, the GUI 324, the vacuum pump 325 and the deflation assembly 326.

In the embodiment illustrated in FIG. 3C, the first deflation initiator inhibitor 354C is in the deactivated state, with the switch toggled to the left. In the deactivated state, the first deflation initiator inhibitor 354C has not been inactivated. Accordingly, the first deflation initiator 353 can be configured to automatically deflate the one or more cryoballoons 331, 332 upon termination of certain stages of the cryoablation procedure. In other words, the deflation of the one or more cryoballoons 331, 332 is not manually controlled.

Figure 4:
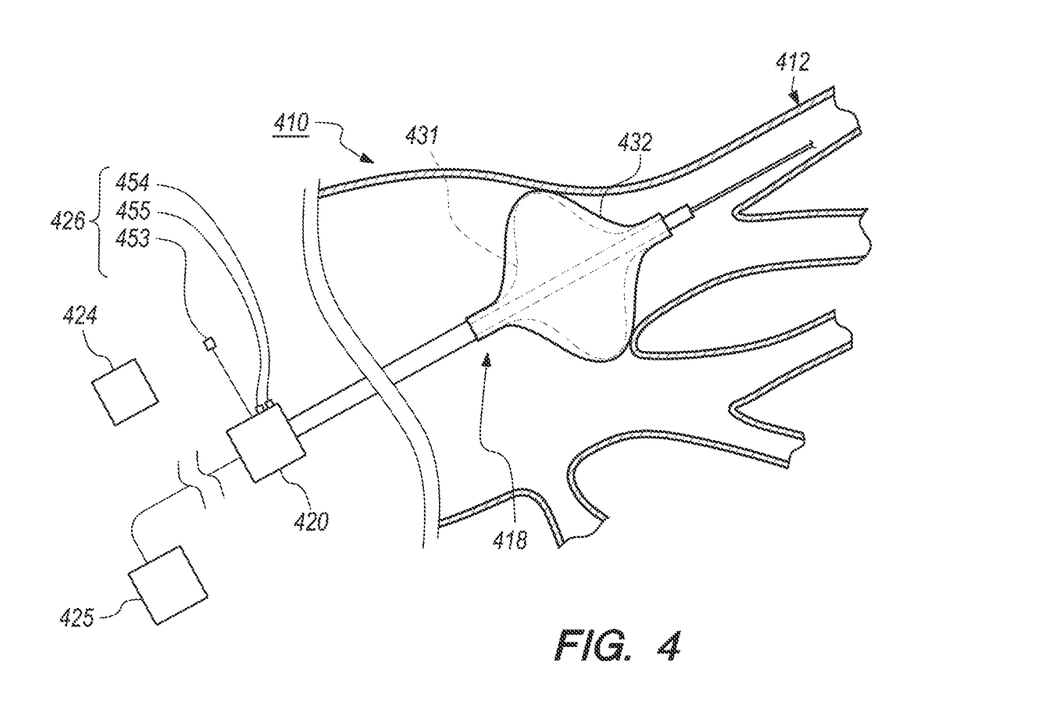
FIG. 4 is a simplified side view of a portion of the patient and a portion of an additional embodiment of the intravascular catheter system including even another embodiment of the cryoballoon deflation assembly.

FIG. 4 is a simplified side view of a portion of the patient 412 and a portion of an additional embodiment of the catheter system 410 including even another embodiment of the deflation assembly 426. In the embodiment illustrated in FIG. 4, the catheter system 410 includes the balloon catheter 418, the handle assembly 420, the GUI 424, the vacuum pump 425 and the deflation assembly 426.

In FIG. 4, the controller 352 (illustrated in FIGS. 3A-3C) is not included as part of the deflation assembly 426. Further, in this embodiment, the first deflation initiator inhibitor 454 includes a control button. In other words, the first deflation initiator inhibitor 454 can be activated or deactivated depending on whether the control button has been depressed. The control button can be positioned, integrated and/or included as part of any other suitable component or structure of the catheter system 410, such as the GUI 424, for example. In this embodiment, the control button is integrated and/or included as part of the handle assembly 420.

In certain embodiments, the first deflation initiator inhibitor 454 can be in the activated state when the control button is depressed (or moved in another suitable manner) by the operator. In the event the control button is depressed, i.e., activated, the first deflation initiator inhibitor 454 can (i) inactivate the first deflation initiator 453, wherein the vacuum pump 425 does not automatically deflate the one or more cryoballoons 431, 432 upon termination of any stage of the cryoablation procedure, and (ii) trigger the second deflation initiator 455.

With the first deflation initiator inhibitor 454 activated, the second deflation initiator 455 can be triggered. As illustrated in this embodiment, the second deflation initiator 455 can also include a control button, wherein in the event the control button is depressed, i.e., activated, the second deflation initiator 455 activates the vacuum pump 425 to initiate deflation of one or more cryoballoons 431, 432.

It is appreciated that the embodiments of the deflation assembly described in detail herein enable the realization of one or more certain advantages when performing multiple ablations during the cryoablation procedure. With the various designs illustrated and described herein, the deflation assembly can decrease procedure times by allowing the operator to selectively and/or manually select whether to initiate elongation of the guidewire lumen and/or to deflate the cryoballoons during the cryoablation procedure. In other words, the operator can select to maintain the cryoballoons partially or fully inflated when performing multiple ablations on the same pulmonary vein, which can decrease the overall time of the cryoablation procedure by eliminating the need to reposition the balloon catheter.

It is understood that although a number of different embodiments of the deflation assembly have been illustrated and described herein, one or more features of any one embodiment can be combined with one or more features of one or more of the other embodiments, provided that such combination satisfies the intent of the present invention.

While a number of exemplary aspects and embodiments of the deflation assembly have been discussed above, those of skill in the art will recognize certain modifications, permutations, additions and sub-combinations thereof. It is therefore intended that the following appended claims and claims hereafter introduced are interpreted to include all such modifications, permutations, additions and subcombinations as are within their true spirit and scope.

I claim:

1. A deflation assembly for an intravascular catheter system for use during a cryoablation procedure, the intravascular catheter system including a vacuum pump and a cryoballoon, the deflation assembly comprising:
   a first deflation initiator that is configured to automatically activate the vacuum pump to deflate the cryoballoon upon completion of a stage of the cryoablation procedure;
   a first deflation initiator inhibitor that is manually changeable between an activated state and a deactivated state, the first deflation initiator inhibitor being configured to inactivate the first deflation initiator when the first deflation initiator inhibitor is in the activated state and to activate the first deflation initiator when the first deflation initiator inhibitor is in the deactivated state;
   a second deflation initiator that is triggered when the first deflation initiator inhibitor is in the activated state, the second deflation initiator including a switch manually changeable between a first position associated with an activated state and a second position associated with a deactivated state, wherein when placed by the switch in the activated state the second deflation initiator activates the vacuum pump to deflate the cryoballoon; and
   wherein the vacuum pump is configured to partially deflate but not fully deflate the cryoballoon when the first deflation initiator inhibitor is in the activated state and the second deflation initiator is in the deactivated state.

2. The deflation assembly of claim 1, wherein the catheter system includes a graphical user interface, and wherein the first deflation initiator inhibitor is configured to be positioned on the graphical user interface.

3. The deflation assembly of claim 2, wherein the first deflation initiator inhibitor includes a switch that moves between a first position and a second position, and wherein only one of the positions of the switch inactivates the first deflation initiator.

4. The deflation assembly of claim 2, wherein the first deflation initiator inhibitor includes a control button that is configured to be depressed.

5. The deflation assembly of claim 4, wherein the first deflation initiator is inactivated when the control button is depressed.

6. The deflation assembly of claim 1, wherein the catheter system includes a control console, and wherein the first deflation initiator inhibitor is configured to be positioned on the control console.

7. The deflation assembly of claim 1, wherein the catheter system includes a handle assembly, and wherein the first deflation initiator inhibitor is configured to be positioned on the handle assembly.

8. The deflation assembly of claim 1, wherein the catheter system includes at least one of a handle assembly, a control console and a graphical user interface, and wherein the second deflation initiator is configured to be positioned on one of the handle assembly, the control console and the graphical user interface.

9. The deflation assembly of claim 1, further comprising a controller, wherein the first deflation initiator inhibitor sends a first signal to the controller to inactivate the first deflation initiator when the first deflation initiator inhibitor is in the activated state.

10. A deflation assembly for an intravascular catheter system for use during a cryoablation procedure, the intravascular catheter system including a graphical user interface, a vacuum pump and a cryoballoon, the deflation assembly comprising:
    a controller;
    a first deflation initiator that is configured to automatically activate the vacuum pump to deflate the cryoballoon upon completion of a stage of the cryoablation procedure;
    a first deflation initiator inhibitor that is configured to be positioned on the graphical user interface, the first deflation initiator inhibitor being manually changeable between an activated state and a deactivated state; wherein the first deflation initiator inhibitor sends a first signal to the controller to inactivate the first deflation initiator when the first deflation initiator inhibitor is in the activated state, and wherein the first deflation initiator inhibitor sends a second signal to the controller to activate the first deflation initiator when the first deflation initiator inhibitor is in the deactivated state;
    a second deflation initiator that is triggered when the first deflation initiator inhibitor is in the activated state, the second deflation initiator including a switch on the graphical user interface manually changeable between a first position associated with an activated state and a second position associated with a deactivated state; wherein when placed by the switch in the activated state the second deflation initiator sends a third signal to the controller to activate the vacuum pump to deflate the cryoballoon when the second deflation initiator is in the activated state; and
    wherein the vacuum pump is configured to partially deflate but not fully deflate the cryoballoon when the first deflation initiator inhibitor is in the activated state and the second deflation initiator is in the deactivated state.

* * * * *